United States Patent [19]
Shetty et al.

[11] Patent Number: 5,877,014
[45] Date of Patent: Mar. 2, 1999

[54] PENICILLIUM STRAIN FOR BIOREMEDIATION

[75] Inventors: Kalidas Shetty; Zuoxing Zheng; Robert E. Levin, all of Amherst, Mass.

[73] Assignee: University of Massachusetts, Boston, Mass.

[21] Appl. No.: 865,223

[22] Filed: May 29, 1997

[51] Int. Cl.$^6$ .............. B09B 3/00; C12N 1/14; A01N 63/00
[52] U.S. Cl. .................. 435/262.5; 435/256.3; 424/93.5
[58] Field of Search ............ 435/262.5, 256.3; 424/93.5

[56] References Cited

U.S. PATENT DOCUMENTS 3,979,283  9/1976  Prudon ........................... 210/11

FOREIGN PATENT DOCUMENTS 62-282696  12/1987  Japan.

OTHER PUBLICATIONS

Chivukula et al.,"Lignin Peroxidase–Catalyzed Oxidation of Sulfonated Azo Dyes Generates Novel Sulfophenyl Hydroperoxides", *Biochemistry*, 34:7765–7772, 1995.

Glenn and Gold, "Decolorization of Several Polymeric Dyes by the Lignin–Degrading Basidiomycete *Phanerochaete chrysosporium*", *Applied and Environmental Microbiology*, 45:1741–1747, 1983.

Gold et al., "Use of Polymeric Dyes in lignin biodegradation Assays", *Methods in Enzymology*, 161:74–78, 1988.

Haemmerli et al., "Oxidation of Benzo(a)oyrene by Extracellular Ligninases of *Phanerochaete chrysosporium*", *The Journal of Biological Chemistry*, 261:6900–6903, 1986.

Katayama and Matusumura, "Degradation of Organochlorine Pesticides, Particularly Endosulfan, By *Trichoderma harzianum*", *Enivronmental toxicology and Chemistry*, 12:1059–1065, 1993.

Knudsen et al., "Method to Enhance Growth and Sporulation of Pelletized Biocontrol Fungi", *Applied and Enivronmental Microbiology*, 57:2864–2867, 1991.

LaCotte et al., "*In vitro* biodegradation of Arabian Light 250 by a marine mixed culture using fertilizers as Nitrogen and Phosphorus sources", *Chemosphere*, 31:4351–4358, 1995.

Nigam et al., "Microbial process for the Decolorization of Textile Effluent Containing Azo, Diazo and Reactive Dyes", *Process Biochemistry*, 31:435–442, 1996.

Paszczynski et al., "Mineralization of Sulfonated Azo Dyes and Sulfanilic Acid by *Phanerochaete chrysosporium* and *Streptomyces chromofuscus*", *Applied and Enivronmental Microbiology*, 58:3598–3604, 1992 Patil et al., Degradation of Endrin, Aldrin, and DDT by Soil Microorganisms, *Applied Microbiology*, 19:879–881, 1970.

Falcon M. A. et al. "Isolation of microorganisms with lignin transformation potential from soil of Tenerife island" Soil Biol. Biochem. vol. 27, No. 2, pp. 121–126, 1995.

Rodriguez A. et al. "Degradation of natural lignins and lignocellulosic substrates by soil–inhibiting fingi impertecti" FEMS Microbiology Ecology 21 (1996) 213–219.

Field J.A. et al. "Biodegradation of polycyclic aromatic hydrocarbons by new isolates of white rot fungi" Appl. Environm. Microbiol. Jul. 1992, pp. 2219–2226.

Grant & Hackh's Chemical dictionary, Fifth Edition, McGraw–Hill Book Company, 1989.

*Primary Examiner*—Sandra E. Saucier
*Assistant Examiner*—Vera Afremova
*Attorney, Agent, or Firm*—Fish & Richardson P.C.

[57] ABSTRACT

A new strain Penicillium Sp.B1 ATCC74414 has been discovered that is capable of degrading polymeric aromatic dyes, including azo dyes. The invention features new Penicillium strains, and mutants thereof, as well as methods of bioremediation to degrade these dyes and other, related aromatic pollutants.

16 Claims, 4 Drawing Sheets

PENICILLIUM STRAIN FOR BIOREMEDIATION

BACKGROUND OF THE INVENTION

The invention relates to a new strain of Penicillium that can be used in bioremediation and to degrade toxic compounds.

Bioremediation is the use of organisms, such as fungi, bacteria, or plants, to degrade pollutants, e.g., in soil, water, or the air. Several fungi are known that degrade organic pollutants. For example, *Phanerochaete chrysosporium* strain BKM-F-1767, Trametes spp., and Bjerkandera adusta are known to degrade polycyclic hydrocarbons, including fluorene and benzo[a]pyrene, and have been investigated for possible use in the bioremediation of contaminated soil and water. In addition, strains of Pseudomonas spp., Alcaligenes spp., Acinetobacter spp., and *Marinobacter hydrocarbonoclasticus* that were isolated from marine sediments contaminated by petroleum were found to degrade Arabian Light crude oil (LaCotte et al., *Chemosphere*, 31:4351, 1995). Pseudomonas spp. and Bacillus spp. can degrade organochlorine pesticides such as DDT, dieldrin, and eldrin (Patil et al., *Appl. Microbiol.*, 19:879, 1970). *Trichoderma harzianum* is known to degrade DDT, dieldrin, endosulfan, and also pentachlorophenol and pentachloronitrobenzene (Katayama and Matsumura, *Environmental Toxicology and Chemistry*, 12:1059, 1993). Trichoderma also produces peroxidases, and two families of this enzyme have been shown to initiate sulfonated azo dye degradation (Chivikula et al., *Biochemistry*, 34:7765, 1995) and oxidation of polycyclic hydrocarbons in vitro (Haemmerli et al., *J. Biol. Chem.*, 261:6900, 1986).

One family of organic pollutants includes the synthetic dyes that are used for textile dyeing, paper printing, color photography, and other industrial applications. Major classes of these synthetic dyes include anthraquinone, azo, and triarylmethane dyes, with azo dyes constituting more than 50% of those used in industrial applications. Many of these dyes are toxic, and discharge of these dye effluents causes serious environmental pollution. Over 0.7 million tons of synthetic dyes are produced annually worldwide, and it is estimated that 10–15% of the dyes are lost in the effluent during use in dyeing processes (Nigam et al., *Process Biochem.* 31:435, 1996). In mammals, the azo linkages are reduced by the intestinal microflora to generate aromatic amines, some of which are potentially carcinogenic (Chivikula et al., *Biochemistry* 34:7765, 1995).

SUMMARY OF THE INVENTION

The invention is based on the discovery of a new strain of Penicillium that is capable of degrading polymeric aromatic dyes, including azo dyes. Thus, the invention features new Penicillium strains, and mutants thereof, as well as methods of bioremediation to degrade these dyes and other, related toxic pollutants, e.g., those that include aromatic rings.

In general, the invention features an isolated, biologically pure culture of a strain of Penicillium, wherein the strain is characterized by the ability to degrade (or discolor) a polymeric, aromatic dye, e.g., Poly R-478 (polyanthraquinone) or Poly S-119. The Penicillium culture can have the identifying characteristics of the Penicillium strain designated herein as G-1, deposited with the American Type Culture Collection and assigned accession number 74414, or mutants thereof, or can be the specific strain having that deposit number.

The invention further features a Penicillium culture composition that includes (a) an isolated Penicillium culture of the invention, e.g., the deposited strain, and (b) a medium that supports growth of the Penicillium culture, wherein the medium and the Penicillium are mixed to form a homogeneous composition. The medium can be a solid, liquid, or semisolid. This composition is useful for bioremediation.

In another aspect, the invention features a method of bioremediation of a polymeric aromatic compound in a substrate, e.g., soil, such as in a landfill, liquid, such as water, or air. Bioremediation is effected by (a) obtaining a medium that will support growth of a Penicillium culture of the invention, (b) inoculating the medium with the Penicillium culture to form a composition, (c) culturing the composition for a time sufficient to allow the Penicillium to grow, and (d) contacting the substrate with the composition for a time sufficient to effect bioremediation of the polymeric aromatic compound. For example, the compound can be a dye, such as a polymeric azo, anthraquinone, or triarylmethane dye. The dye can be Poly R-478 (polyanthraquinone) or Poly S-119.

The compound to be bioremediated can be a hydrocarbon, petrochemical, phenol, hydroquinone, benzoquinone, nitrotoluene, fluorene, or a benzo[a]pyrene. In addition, the compound can be a pesticide, e.g., DDT, dieldrin, endosulfan, pentachloronitrobenzene, or pentachlorophenol.

The invention also features a method of degrading a polymeric aromatic dye, e.g., a polymeric azo, anthraquinone, or triarylmethane dye, in a substrate, by (a) obtaining a medium that will support growth of a Penicillium culture of the invention, (b) inoculating the medium with the Penicillium culture to form a composition, (c) culturing the composition for a time sufficient to allow the Penicillium to grow, and (d) contacting the substrate with the composition for a time sufficient to degrade the polymeric, aromatic dye.

"Bioremediation" is the use of organisms to degrade undesirable compounds from a substrate.

An "azo dye" is any dye that includes an azo group.

An "active mutant" of the G-1 strain is a naturally occurring or man-made mutant of the G-1 strain that has at least 50 percent of the polymeric aromatic dye degrading capability of the G-1 strain.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

The invention provides a new fungal strain that can be used for simple and cost-effective bioremediation and removal of toxic compounds from various substrates including soil and water.

Other features and advantages of the invention will be apparent from the following detailed description, and from the claims.

DETAILED DESCRIPTION

Figure 1:
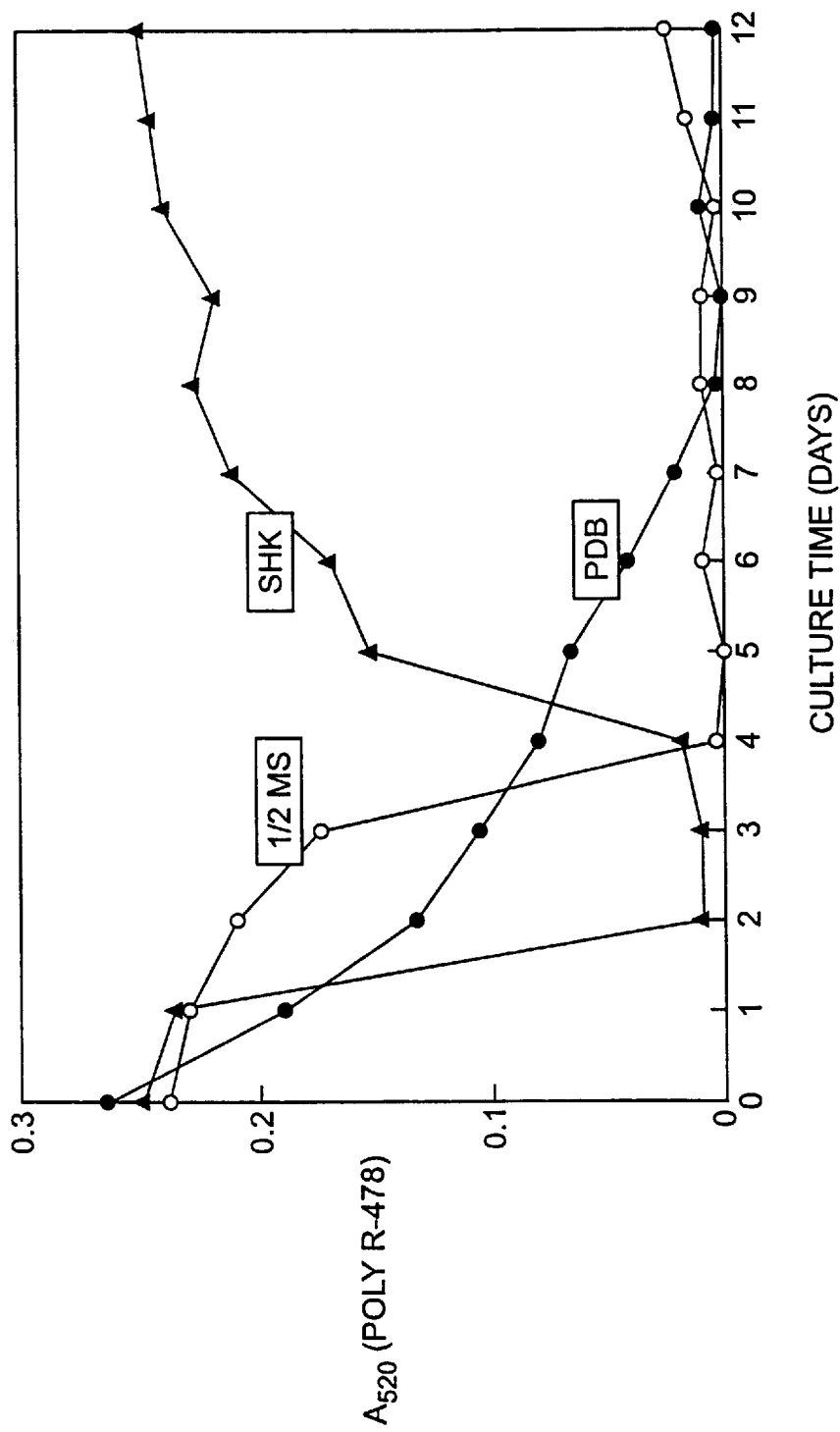
FIG. 1 is a graph illustrating decolorization of 0.01% polymeric dye Poly R-478 by Penicillium strain G-1 in three different liquid media over twelve days.

Bioremediation is the use of organisms, such as fungi, bacteria, or plants, to remove toxins and pollutants from substrates such as soil, water, or air. In general, synthetic dyes are not readily degraded by microorganisms (Paszczynski et al., 1992, *Appl. Environ. Microbiol.*, 58:3598), but a number of aerobic and anaerobic organisms have been demonstrated to degrade some dyes (Nigam et al., *Process Biochem.*, 31:435, 1996; Chivikula et al., *Biochem.*, 34:7765, 1995; Field et al., *Appl. Environ. Microbiol.*, 58:2219, 1992; Glenn and Gold, *Appl. Environ. Microbiol.*, 45:1741, 1983). In fact, decolorization of polymeric aromatic dyes is an indicator of the lignin-degrading ability of fungi (Glenn et al., *Methods Enzymol.*, 161:74, 1988). Lignin-degrading ability in turn has been found to be an indicator of the ability to break down chlorophenols, nitrotoluenes, polycyclic aromatic hydrocarbons, dioxins, fluorene, and benzo[a]pyrene (Chivikula et al., *Biochem.*, 34:7765, 1995; Haemmerli et al., *J. Biol. Chem.*, 261:6900, 1986).

In particular, the rate of decolorization of the dye Poly R-478 has been correlated with the rate of degradation of the polycyclic aromatic hydrocarbons anthracene and benzo[a] pyrene (Field et al., *Appl. Environ. Microbiol.* 58:219, 1992). Therefore, fungi that can degrade these synthetic polymeric aromatic dyes can also be used to degrade other pollutants, e.g., chlorophenols, nitrotoluenes, polycyclic aromatic hydrocarbons such as anthracene and benzo[a] pyrene, dioxins, fluorene, and benzo[a]pyrene.

The invention is based on the discovery of a new strain of Penicillium, G-1, which degrades polymeric aromatic dyes, including azo dyes, and other organic aromatic pollutants, making it useful in various methods of bioremediation. The G-1 strain was isolated from tissue cultures of anise (*Pimpinella anisum*), and grows well on potato dextrose agar or trypticase soy agar. G-1 has green, or sometimes blue-green, conidiospores with biverticillate metulae. Strain G-1 is typical of the Penicillium genus, but constitutes an as yet unique and unnamed species. It decolorizes two polymeric aromatic dyes, Poly R-478™ (polyanthraquinone; poly(vinylamine) sulfonate backbone with anthrapyridone chromophore) and Poly S-119™ (poly(vinylamine) backbone with azo chromophore), in liquid media containing 0.01% of those dyes.

This decolorization ability was not observed in other known Penicillium species that were tested and compared. When grown in three different media containing the dyes, strain G-1 was found to decolorize and degrade Poly S-119. G-1 also decolorized and degraded R-478 in two of the media, but when grown in the third, it decolorized but then released the dye back into the medium after 2 to 3 days, indicating that the initial decolorization of the media was due to absorption of the dye, with no subsequent degradation. The ability of G-1 to degrade Poly R-478™ and Poly S-119™ indicates that it can degrade other pollutants.

Isolation and Characterization of the G-1 Strain

The G-1 strain was serendipitously discovered during a study of the dye-degrading ability of a series of anise (*Pimpinella anisum*) root cultures. During this study, one root culture was found to completely degrade the dye Poly R-478. Further investigation showed that a greenish contaminant was responsible for the dye degradation, rather than the root culture itself. This substance was further isolated and identified as follows.

Identification

This Poly R-478-degrading Penicillium strain was tentatively named G-1 because it produced green spores on a petri plate. Additional morphological and cultural characteristics were determined with the use of Mycological Agar, YM Agar, Sabourauds Agar, Wort Agar, Orange Serum Agar and Czapek Agar media for the preparation of giant colonies and Henrici media slide preparations (*Molds, Yeasts, and Actinomycetes,* Wiley and Sons, New York, 1930). Giant colonies were examined with the naked eye and low powers of a compound microscope. Details of structure were observed with the use of microscope at magnifications of 510× to 1,400×. Carbon and nitrogen source utilization was determined with the use of Yeast Nitrogen/Carbon Base, washed cells, purified agar, and the auxanographic plate technique (Ramirez, *Manual and Atlas of the Penicillia*, Elsevier Biomedical Press, Amsterdam, The Netherlands, 1982). Morphological and physiological growth characteristics of the new isolate were compared to current information on Penicillium (Ramirez, *Manual and Atlas of the Penicillia*, Elsevier Biomedical Press, Amsterdam, The Netherlands, 1982; Raper et al., *A Manual of the Penicillia*, The William & Wilkins Co., Baltimore, Md., USA, 1949).

Morphological Characterization

As has been outlined by Raper et al. (*A Manual of the Penicillia*, The William & Wilkins Co., Baltimore, Md., USA, 1949), the taxonomy of the genus Penicillium is based primarily on the cultural and morphological characteristics of colonies grown on standardized agar media (see also, Ramirez, *Manual and Atlas of the Penicillia*, Elsevier Biomedical Press, Amsterdam, The Netherlands, 1982). The colony formed by new isolate G-1 on a PDA petri plate exhibited typical Penicillium characteristics. These included white woolly floccose mycelium turning to blue-green on formation of conidiospores, velvety and fairly compact texture, slightly spreading and wrinkled growth habit.

Microscopic observations established certain structural characteristics, including the penicillus structure which is typical to genus Penicillium, and the typical chain of conidiospores. Characters unique to G-1 included the dual metula (biverticillate, two metulae per conidiophore), and that each metula had 4 to 5 clusters of single elongated phialides on which chains of conidia branched, forming a brush-like mass. The conidiospores were olive shaped and in long chains. These morphological characteristics indicated that the new isolate G-1 belongs to genus Penicillium, but its species designation was not made at this time. Although it appears close to one or two Penicillium species, the unique features of G-1 suggest that it might be a unique species and possibly requires a new species designation.

Giant Colony Characteristics

The new isolate G-1 was incubated at 32° C. for 8 days following inoculation of a ¼ inch diameter zone at the center of petri plates with various classical fungal culture media. The characteristics of the giant colony formed on each plate with different media is summarized in Table 1.

TABLE 1

Giant Colony Characteristics of Penicillium G-1

| Medium | Characteristics |
| --- | --- |
| Mycological Agar | 75 mm diameter zone of growth; 30 mm diameter central dark gray zone of conidiospores; 7 mm white peripheral margin of mycelium; Mouse gray color of conidiospores; Rear of colony: pale yellow and smooth; |
| YM Agar | 80 mm diameter zone of growth; 45 mm diameter central mouse gray zone of conidiospores; 5 mm white peripheral margin of mycelium; 5 mm blue-gray ring of conidiospores just internal to white outer margin of mycelium; Rear of colony: pale yellow and smooth; |
| Sabourauds Agar | Blue-gray conidial zone beyond central diameter of 45 mm; Exudate droplets of 40 mm diameter in center zone; 66 mm blue-gray zone and 6 mm white outer peripheral zone of mycelium; Rear of colony: light tan and smooth; |
| Wort Agar | Smooth gray and velvet conidial growth; Hexagonal shape of colony with parallel sides 49 mm distant; Central zone of 20 mm diameter dark gray; Rear of colony: pale yellow with 6 deep wrinkles; |
| Orange Serum Agar | 74 mm diameter zone of growth; Light gray color of conidiospores; 35 mm diameter central darker zone with concentric rings; Mycelial mat of radiating wrinkles; Rear of plate: yellow/buff with 52 spoked wrinkles |
| Czapek Agar | 48 mm diameter zone of growth; Green (olive drab) color of conidiospores; Outer margin of 2 mm white mycelial mat of radiating wrinkles; Rear of colony: light buff and wrinkled |

Growth Parameters and Carbon/Nitrogen Source Utilization

On Orange Serum Agar medium, the new isolate grew at 10° C., 20° C., 32° C. and 37° C., but not at 4° C. To test the carbon source utilization, auxanographic plates were prepared with washed cell, Yeast Nitrogen Base, and purified agar. The growth results showed that the Penicillium isolate was able to utilize a fairly diverse spectrum of carbon sources. These included dextrin, dextrose, fructose, galactose, inositol, sorbitol, sucrose, xylose, melibiose, melezitose, β-galacturonic acid, mannose, mannitol, maltose, esculin, cellobiose, arabinose, arabitol and salicin. However, it did not utilize starch, inulin, dulcitol, adonitol, and fucose. The new isolate was able to utilize nitrate as the nitrogen source.

G-1 Mutant Strains

Mutants of the G-1 strain can be made using techniques that are well known in this field. For example, an asporogenous mutant can be obtained through ethylmethane sulfonate (EMS) mutagenesis of G-1. The mutants can also be made using ultraviolet light or nitrosoguanidine using standard techniques.

Recombinant Microorganisms Containing G-1 Strain Genes

Novel recombinant microbes containing genes from the G-1 strain, and active mutants thereof, can be made by isolating gene(s) from G-1, and transforming a suitable host with the gene(s). In particular, genes that encode enzymes capable of degrading polymeric aromatic dyes can be used to prepare recombinant microorganisms that produce these specific enzymes, which are useful for bioremediation of polymeric aromatic dyes, and related aromatic pollutants.

Many ways are known for introducing a gene into a host microorganism under conditions that allow for stable maintenance and expression of the gene. One can provide DNA constructs that include the transcriptional and translational signals for expression of the gene, replication or integration sequences, promotor sequences, or marker genes. Such sequences may come from a wide variety of organisms, such as the host organism, bacteria, bacteriophage, cyanobacteria, fungi, algae, or viruses, and are well known in the art. The construct can be in a plasmid, or can be intended to be incorporated into the genome of the host. The host can be a bacterium, fungus, algae, or any of a number of host organisms known in the art. The transformed host cells can be cultured in the media most appropriate to their growth, and the desired products, such as enzymes, isolated and purified using standard techniques.

G-1 Lysates

The invention can also be practiced by using a lysate of the G-1 strain, or an active mutant thereof. The lysate can be produced from cultures of the G-1 strain by culturing sufficient quantities of the microbes, isolating the microbes from the culture medium, and then preparing a lysate by mechanical means (e.g., grinding), chemical or biochemical means (e.g., cellulase), or other means (e.g., ultrasound). The lysate can be used for bioremediation in the same way as compositions containing living Penicillium cultures.

Identifying Characteristics

The Penicillium G-1 strain, and active mutant strains thereof, can be distinguished from other Penicillium strains by any one or more of the following identifying characteristics: (1) these strains degrade Poly R-478 (0.01%) in liquid HMS medium by at least 90% within four days; (2) these strains degrade Poly R-478 (0.01%) in liquid PDB by at least 90% within eight days; (3) these strains degrade Poly S-119 (0.01%) in liquid SHK, HMS, or PDB media by at least 80% within three days; (4) these strains exhibit dual metula, each with 4 to 5 clusters of single elongated phialides; and (5) these strains exhibit a brush-like mass formed by the conidia.

Bioremediation

The new Penicillium strain G-1, and active mutants thereof, can be used to degrade polymeric aromatic dyes, including azo dyes, and other aromatic pollutants such as chlorophenols, nitrotoluenes, polycyclic aromatic hydrocarbons, e.g., anthracene and benzo[a]pyrene, dioxins, fluorene, and benzo[a]pyrene in a contaminated substrate, e.g., soil, sand, water, or air. In general, bioremediation is accomplished by obtaining a composition including growth media, such as potato dextrose medium, trypticase soy medium, or other fungal media, and a viable culture of the G-1 strain, and adding an effective amount of that composition to the contaminated substrate for a time sufficient to effect degradation of the contaminant.

For example, G-1 and active mutants thereof can be grown on a large scale on a medium such as apple pomace (the waste product left behind after apple processing), as described in Example 3 below, or other medium. Such large scale growth can be carried out in a rotating-drum bioreactor, such as the one shown in FIG. 4. Bioreactor 10 includes a drum 12, made of steel or glass, that contains an apple pomace or other medium 11. The drum 12 rests on its side on two rollers 13, and is driven by motor 16 via a belt or chain 17, rotating on central axis 18 in the direction of rotation shown by arrow 20. The inner wall of drum 12 includes three curved mixing vanes 14 running lengthwise on the inside of the drum. The vanes are slightly cupped so that as the drum rotates, a portion of the medium 11 is carried upward, and is dropped when the vane approaches its uppermost position. The drum 12 holds a specific amount, e.g., ten liters, of the medium. The drum is rotated slowly (e.g., 2–5 revolutions per minute) and provides mixing of composition ingredients, distribution of microbial inoculum, sufficient aeration for microbial growth and colonization, and adequate mixing to provide a homogeneous composition. The simple design of the bioreactor allows it to be scaled up for larger batches and it can be constructed of easily obtained materials.

Maximum growth of a given microorganism is generally achieved in five to seven days, or when the entire medium appears green with conidia. Scale-up to the bioreactor is done stepwise with inoculation from an agar slant of purified strains, into 100 milliliter flask culture for 4 days. These small cultures are then used to inoculate larger 2 to 4 liter cultures, which after 4 to 5 days are used to inoculate the large bioreactor described above. A bioreactor full of inoculum can be made from an agar slant in two to three weeks.

For bioremediation of a contaminated liquid substrate such as water, the liquid can be run through a column packed with the medium mixed 1:1 with clean soil or other inert material. For bioremediation of a contaminated solid substrate such as soil or sand, the medium can be tilled directly into the contaminated substrate. Polluted gases, such as air, can be bubbled through liquid medium containing G-1, or drawn through a filter upon which the G-1 is grown.

The G-1 strain can also be made into a dry, pelletized form for easier distribution and storage. Such methods are described in Knudsen et al. (*Appl. Environ. Microbiol.* 57:2864, 1991), and are well known in the agricultural industry. For example, sodium alginate solution in demineralized water is prepared at a concentration of 2% (weight/volume) and autoclaved at 121° C. for 10 minutes. Equal parts of the sodium alginate solution and the G-1-inoculated apple pomace (or G-1 in other media) are mixed to achieve a final concentration of 1% sodium alginate. The mixture is then extruded dropwise out of a sterile needle into 0.1 molar $CaCl_2$ (aqueous solution) to form beads or pellets. These pellets are removed from the solution by screening, and dried at 22°–25° C.

The dried pellets can be stored, transported, or used as is, but growth of the fungi is significantly increased by a subsequent treatment of the dried pellets by soaking in 40% polyethylene glycol (aqueous solution) for 16 hours at 22° C., followed by an additional air drying. This pelletized form can be tilled directly into contaminated soil and hydrated by watering, or mixed into contaminated liquid. Specific amounts to be used vary based on the pollution conditions at each site. Application and monitoring of results must be carried out on a case-by-case basis by professionals trained in toxic waste detection and removal.

The invention will be further described in the following examples, which do not limit the scope of the invention described in the claims.

EXAMPLES

Example 1

Degradation of Poly R-478 and Poly S-119 by G-1 Culture Media

All fungi were maintained and subcultured on potato dextrose agar (PDA) slants or plates prior to inoculation into liquid media. The liquid media included HMS (half MS-salts and hormone free medium) which was a revised medium based on Murashige and Skoog (MS) medium (Murashige and Skoog, *Physiol. Plant.* 15:473, 1962), SHK medium which was based on Schenk and Hildebrandt medium (*Can. J. Bot.* 50:199, 1972) and revised by Shetty and McKersie (*Plant Science* 88:185, 1993), and PDB (potato dextrose broth). The HMS and SHK media were originally formulated for use as plant tissue culture media, while PDB is a common fungal culture medium. The HMS medium consisted of 2.17 milliliters of MS-salts, 5 milliliters of N,N-vitamins and 15 grams of sucrose per liter, adjusted to a pH of 5.8. The SHK medium consisted of 3.2 grams of salts, 10 milliliters of N,N-vitamins, 1.74. grams of $K_2SO_4$, and 30 grams of sucrose per liter with a final pH of 5.8.

Incubation Conditions

The PDA plates were incubated statically at 30° C. for one week before use. Erlenmeyer flasks (125 milliliter) containing 50 milliliters of liquid medium were inoculated with approximately $10^7$ conidia spores and incubated at 30° C. in aerobic conditions on a shaker at 150 rpm for 3–12 days.

Decolorization Assay

Polymeric dyes Poly R-478™ (polyanthraquinone) and Poly S-119™ were measured spectrophotometrically by absorbance at 520 and 472 nanometers, respectively. They were added to the liquid medium as an aqueous solution to a final concentration of 0.01% (weight/volume) before autoclaving. Directly after autoclaving and at the indicated intervals of incubation, 0.5 milliliters of the extracellular culture medium was removed and diluted 10-fold with distilled water, and the absorbance was measured. In most cases, the mycelia grew into ball-shaped masses in the liquid medium, and it the liquid aliquots could be removed without centrifugation or filtration. If the liquid sample was turbid, it was necessary to centrifuge and filter it before measuring the absorbance. The uninoculated medium was used as a control, and medium without dyes was used as blank.

This decolorization assay can be used to test Penicillium strains related to G-1 that have the same decolorization, and hence degradation, effect, on polymeric aromatic dyes, and to test G-1 mutants to determine whether they are active mutants.

Decolorization of Poly R-478 by G-1

The new isolate was able to grow in HMS, SHK, and PDB media and decolorization was observed in all three liquid systems. The results are shown in FIG. 1, which is a graph illustrating the spectrophotometric absorbance (in nanometers) of the cultures over 12 days.

In both the HMS and PDB media, decolorization was complete and permanent, with no release of the dye back into the medium, indicating that G-1 degraded of the polymeric aromatic Poly R-478 dye. Decolorization was nearly complete on HMS medium at day 4, while on PDB medium, decolorization was more gradual, and complete at about eight days of incubation.

Decolorization in the SHK medium occurred at a very rapid rate in the first 2 to 3 days, falling to nearly zero, but at day 4, the absorbance began to rise until it reached initial levels at 10 days of incubation, indicating that the mycelial mass absorbed the dye initially, but then released it back into the medium. Microscopic observation revealed that in SHK medium, the mycelial mass absorbed the Poly R-478 and turned pink, but then turned white again when the dye was released back into the medium. This is in contrast to the behavior of G-1 with this dye in the other media, in which the mycelial mass was seen to turn pink as the dye was absorbed, then white as the dye was degraded, with no release back into the medium.

The fact that media selection had an effect on the decolorization of Poly R-478 by G-1 is probably due to the organism's use of different metabolic pathways on the different media, and that some of these pathways utilize the dye as a carbon source, while others may not.

Decolorization of Poly S-119 by G-1

Figure 2:
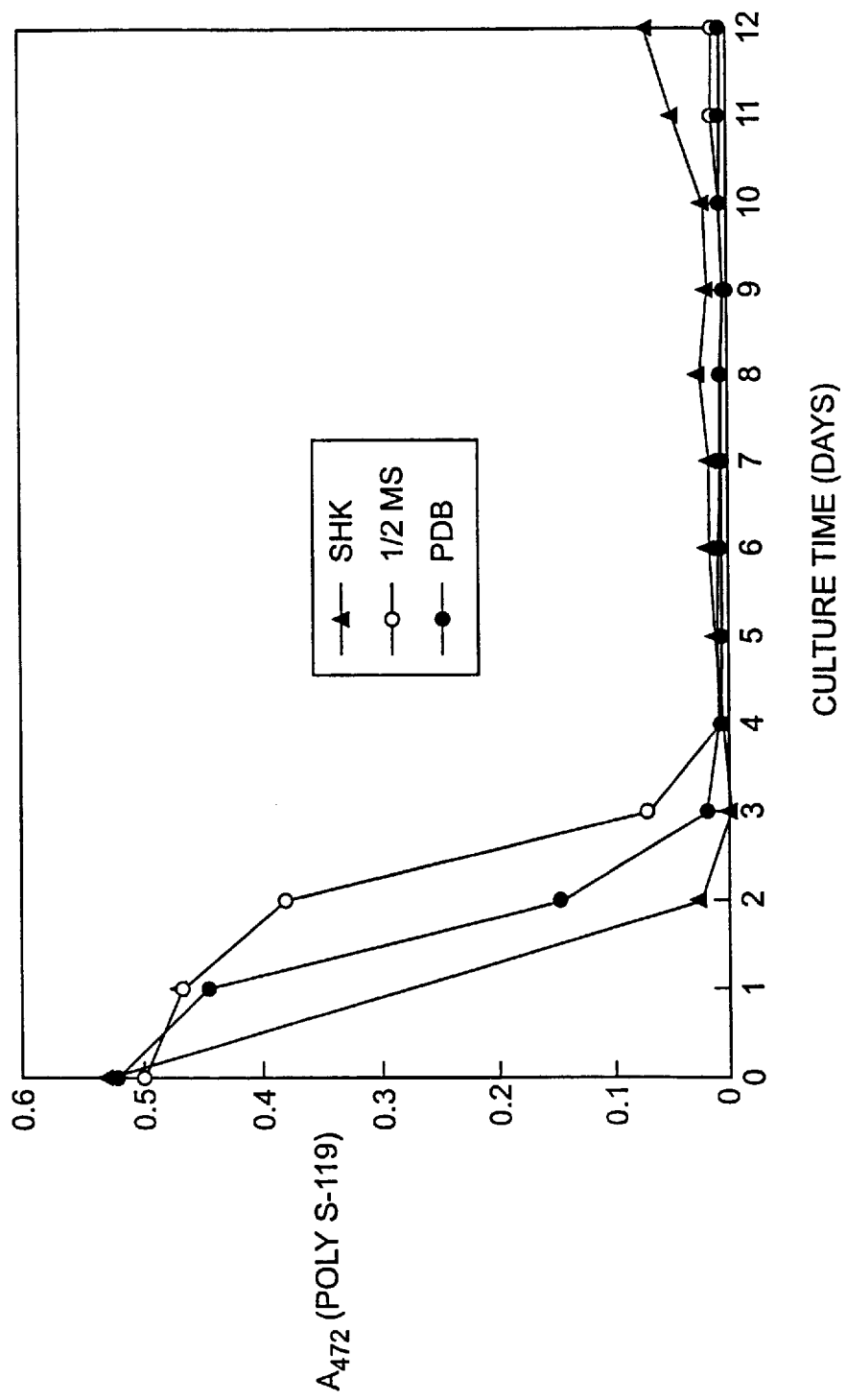
FIG. 2 is a graph illustrating decolorization of 0.01% polymeric dye Poly S-119 by Penicillium strain G-1 in three different liquid media over twelve days.

When polymeric dye Poly S-119 was added to HMS, SHK, or PDB medium, the G-1 strain was able to completely decolorize Poly S-119 in 3 to 4 days, as shown in FIG. 2, which is a graph illustrating the spectrophotometric absorbance (in nanometers) of the cultures over 12 days. When G-1 was grown in SHK medium, decolorization of Poly S-119 was almost complete at 2 days, and fully complete at 3 days of incubation. In both HMS and PDB media, decolorization took one day longer than on SHK medium.

Unlike Poly R-478, Poly S-119 was fully decolorized in SHK medium by G-1, and no subsequent release of Poly S-119 from the mycelial mass back to the medium was observed. Thus, G-1 degraded the polymeric aromatic Poly S-119 dye.

Example 2
Degradation of Dye Poly R-478 by Other Fungi

To compare the ability of decolorization by the new isolate to other related fungi, six fungal strains were tested for their ability to decolorize Poly R-478 in HMS medium. These included *Penicillium vermiculatum* (PV), *Penicillium chrysogenum* (PC), Penicillium P-1 (a good pigment-producer), *Trichoderma viride* IF-26 (TV), *Trichoderma harzianum* ATCC 24274 (TH), and *Trichoderma pseudokoningii* ATCC 26801 (TP). The Trichoderma species were selected because some species in this genus are known to degrade aromatic pollutants (*Katayama and Matsumura, Environmental Toxicology and Chemistry*, 12:1059, 1993).

Figure 3:
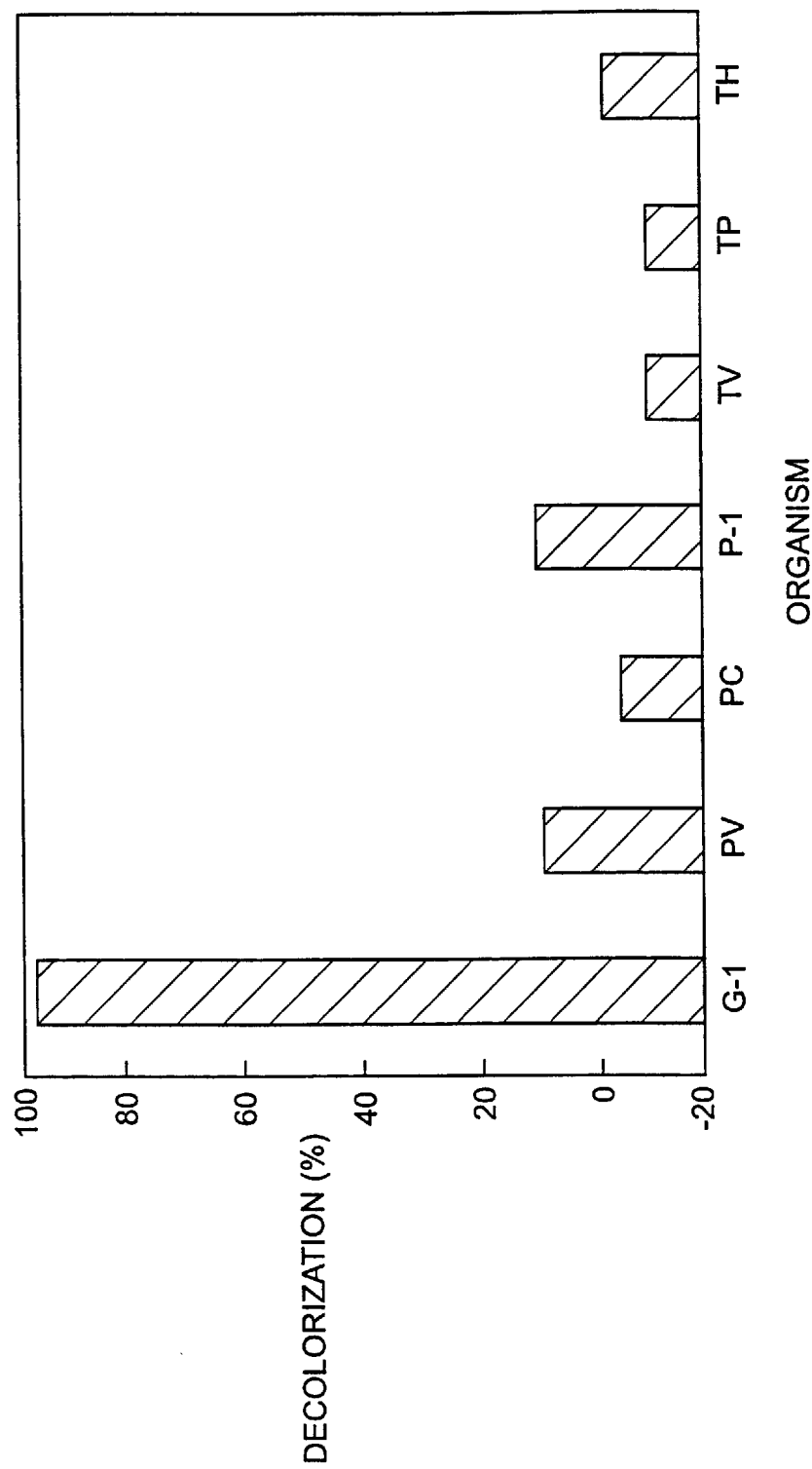
FIG. 3. is a bar graph illustrating decolorization of 0.01% polymeric dye Poly R-478 in HMS medium by G-1 and six other organisms after four days of incubation.

Conditions used were the same as in Example 1. The results are shown in FIG. 3, which is a bar graph showing the percent decolorization of 0.0% Poly R-478 in HMS medium after four days of incubation. G-1 showed nearly 100% decolorization, while all of the other strains showed little or no decolorization. This suggests that the new isolate G-1 is a unique Penicillium species that can degrade polymeric aromatic dyes, and thus other related aromatic pollutants.

Example 3
Large Scale Growth of Penicillium Strain G-1

Figure 4:
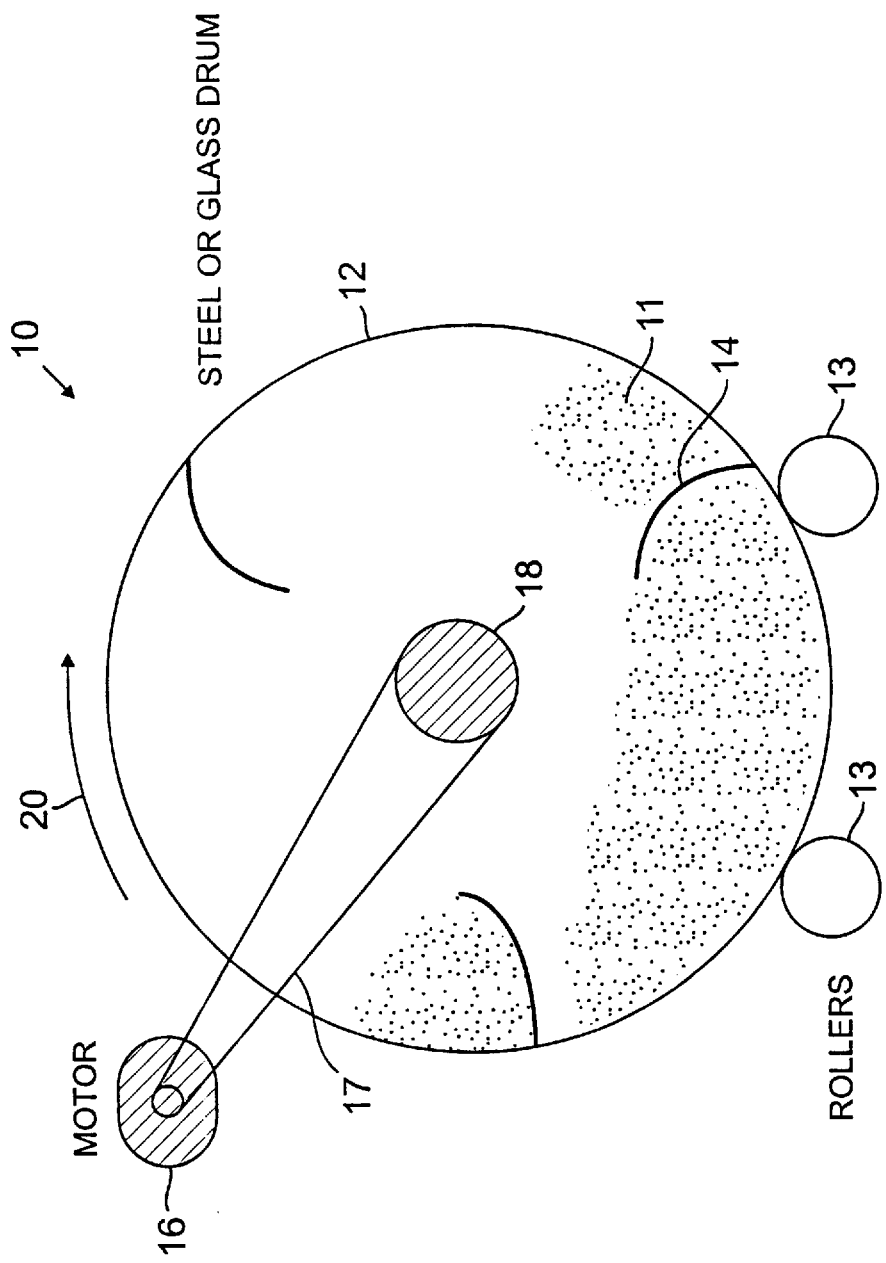
FIG. 4 is a schematic diagram in cross-section, illustrating a ten-liter rotating drum bioreactor for large-scale production of Penicillium strain G-1 cultures.

125-milliliter flasks containing 10 grams of apple pomace (the solid waste left behind after apple processing), 25 milliliters of water, 0.5 grams of $CaCO_3$, and 0.5 grams of $NH_4NO_4$ were inoculated with spores from Penicillium strain G-1, which was stored on potato dextrose agar. After five days of incubation at room temperature without agitation, the cultures were then used to inoculate 2-liter batches of the same culture medium. After 5 days of incubation, the 2-liter cultures were used to inoculate 10 liters of the apple pomace medium in a bioreactor (FIG. 4). The bioreactor drum is rotated slowly (2–5 revolutions per minute), and provides sufficient aeration for microbial growth and colonization. In fourteen days, 10 liters of Penicillium strain G-1 is ready to be mixed with contaminated liquid or tilled directly into contaminated soil.

Deposit

Under the terms of the Budapest Treaty on the International Recognition of the Deposit of microorganisms for the Purpose of Patent Procedure, deposit of the Penicillium strain G-1 was made with the American Type Culture Collection (ATCC) of 12301 Parklawn Drive, Rockville Md., USA, on May 29, 1997, and bears the accession number 74414. The deposit has been made under conditions that assure that access to the cultures will be available during the pendency of the patent application disclosing them to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A biologically pure Penicillium culture having all identifying characteristics of the Penicillium strain deposited with the American Type Culture Collection and assigned accession number 74414, or active mutants thereof.

2. A biologically pure culture of Penicillium strain G1 deposited with the American Type Culture Collection and assigned accession number 74414, or active mutants thereof.

3. A Penicillium culture composition comprising (a) an isolated Penicillium culture of claim 2, and (b) a medium that supports growth of said Penicillium culture, wherein the medium and the Penicillium are mixed to form a homogeneous composition.

4. The composition of claim 3, wherein the medium is a solid.

5. The composition of claim 3, wherein the medium is a liquid.

6. A method of bioremediation of a compound in a substrate, the method comprising (a) obtaining a medium that will support growth of the Penicillium culture of claim 2, (b) inoculating the medium with the Penicillium culture to form a composition, (c) culturing the composition for a time sufficient to allow the Penicillium to grow, and (d) contacting the substrate with the composition for a time sufficient to effect bioremediation of the compound.

7. The method of claim 6, wherein the compound is a dye.

8. The method of claim 7, wherein the dye is a polymeric azo, anthraquinone, or triarylmethane dye.

9. The method of claim 7, wherein the dye is Poly R-478 (polyanthraquinone) or Poly S-119.

10. The method of claim 6, wherein the substrate is soil.

11. The method of claim 6, wherein the substrate is a liquid.

12. The method of claim 6, wherein the substrate is air.

13. The method of claim 6, wherein the compound is selected from the group consisting of hydrocarbons, petrochemicals, phenols, hydroquinones, benzoquinones, nitrotoluenes, fluorenes, and benzo[a]pyrenes.

14. The method of claim 6, wherein the compound is a pesticide.

15. The method of claim 14, wherein the pesticide is DDT, dieldrin, endosulfan, pentachloronitrobenzene, or pentachlorophenol.

16. The method of claim 6, wherein the substrate is landfill.

* * * * *